United States Patent [19]

Noda et al.

[11] 4,228,304
[45] Oct. 14, 1980

[54] NOVEL CYCLOHEXANECARBOXYLIC ACID AND ITS DERIVATIVES

[75] Inventors: Kanji Noda, Chikushino; Akira Nakagawa; Kenji Yamagata, both of Tosu; Terumi Hachiya, Chiyoda; Hiroyuki Ide, Fukuoka; Akihide Koda, Gifu, all of Japan

[73] Assignee: Hisamitsu Pharmaceutical Co. Inc., Saga, Japan

[21] Appl. No.: 895,485

[22] Filed: Apr. 11, 1978

[30] Foreign Application Priority Data

Jun. 16, 1977 [JP] Japan ................... 52-72639

[51] Int. Cl.³ .............................. C07C 103/50
[52] U.S. Cl. ..................... 562/507; 560/125; 562/400; 562/438; 562/450; 424/305; 424/309; 424/319
[58] Field of Search ............... 260/514 R, 514 J; 560/1, 125; 562/507, 400, 450, 435

[56] References Cited

U.S. PATENT DOCUMENTS 3,683,040  8/1972  Knowles ............... 260/668 R
4,150,052  4/1979  Watson et al. ......... 26/557 R Primary Examiner—Robert Gerstl
Attorney, Agent, or Firm—Browdy and Neimark

[57] ABSTRACT

The present invention relates to novel cyclohexanecarboxylic acid and its derivatives represented by the general formula:

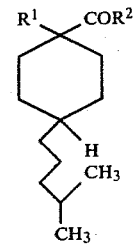

(wherein $R^1$ is selected from the group consisting of hydrogen or methyl; $R^2$ is selected from the group consisting of hydroxyl, lower alkoxy with 1-6 carbons or amino acid rest. In case $R^1$ is hydrogen, however, $R^2$ means amino acid rest, which of all the compounds of the present invention are entirely novel ones which have never been in any printed publications, possessing a high degree of pharmacological activities such as anti-allergic, anti-inflammatory, anti-ulcerative, antibacterial, anti-thrombotic and liver-function-improving activities, and therefore, these compounds are useful as medicines, and besides, these compounds are surface-active and, therefore, useful as additives for toothpaste and shampoo, as surface active agents for detergents, dispersing agents, emulsifying agents and cosmetics, as anticarious agents, and also in industrial fields the aforesaid compounds are useful as detergents for keeping textiles soft, as additives for lubricating oil, as anti-rust agents, additives for plastics and also as metal-capturing agent, ion-floating agents and emulsifying agents for other industrial purposes).

3 Claims, No Drawings

NOVEL CYCLOHEXANECARBOXYLIC ACID AND ITS DERIVATIVES

DETAILED DESCRIPTION

The present invention relates to novel cyclohexanecarboxylic acid and its derivatives represented by the following general formula (I):

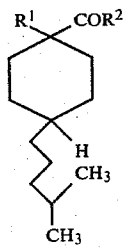

(wherein $R^1$ is selected from the group consisting of hydrogen or methyl; $R^2$ is selected from the group consisting of hydroxyl, lower alkoxy with 1-6 carbons or amino acid rest. In case $R^1$ is hydrogen, however, $R^2$ means amino acid rest.)

All the compounds of the present invention are entirely novel ones which have never been in any printed publications, possessing a high degree of pharmacological activities such as anti-allergic, anti-inflammatory, anti-ulcerative, antibacterial, anti-thrombotic and liver-function-improving activities. Therefore, these compounds are useful as medicines.

Besides, these compounds are surface-active and, therefore, useful as additives for toothpaste and shampoo, as surface active agents for detergents, dispersing agents, emulsifying agents and cosmetics, and also as anticarious agents. In industrial fields the aforesaid compounds are useful as detergents for keeping textiles soft, as additives for lubricating oil, as anti-rush agents, additives for plastics and also as metal-capturing agent, ion-floating agents and emulsifying agents for other industrial purposes.

$R^2$ in the aforesaid general formula I is described hereinafter. $R^2$ is selected from the group consisting of hydroxyl and lower alkoxy with 1-6 carbons or amino acid rest. A concrete explanation concerning the aforesaid $R^2$, lower alkoxy may be methoxy, ethoxy, propoxy, butoxy, pentyloxy and hexyloxy, and amino acid of amino acid rest may be acidic amino acid such as glutamic acid, aspartic acid, α-aminoadipic acid, α-aminopimelic acid, glutamine, cysteic acid, homocysteic acid and 2-amino-eicosandicarboxylic acid or those of lower alkyl ester; neutral amino acid such as glycine, phenylalanine, phenylglycine, alanine, α-aminobutyric acid, valine, norvaline, leucine, isoleucine, norleucine, p-nitrophenylalanine, tryptophan and proline or those of lower alkyl ester; amino acid having sulfur atoms such as methionine, cystein, homocystine, penicillamine and ethionine or those of lower alkyl ester; amino acid having hydroxyl group such as threonine, serine, tyrosine, nitrotyrosine, β-hydroxyleucine, homoserine and oxyproline; N-methyl or N-ethyl derivatives of α-amino acid such as sarcocine; o-acyl or o-methyl derivatives of amino acid having hydroxyl group such as serine; $N^\omega$, $N^\omega$-dilower alkyl derivatives of basic amino acid such as lysine and ornithine; and β-amino acid such as β-alanine and β-aminoisobutyric acid; and ε-amino acid such as γ-aminovalearic acid, ε-aminocaproic acid and those of N-methyl or N-ethyl derivatives. It is no matter whether the aforesaid amino acid and its derivatives are in the form of optically active body or raceme.

The compounds I of this invention may be led to the production of inorganic base such as sodium, potassium and calcium, and also organic base such as monoethanolamine, diethanolamine and triethanolamine.

Hitherto, adrenocortical hormone alone has been known as anti-allergic agents, especially those of delayed type. However, steroid preparations cause serious side-effects if administered continuously for a long period of time and, therefore, the development of non-steroid anti-allergic agents with less side-effects is in demand. The present inventors synthesized cyclohexanecarboxylic acid and its derivatives represented by the general formula I in search of novel compounds of non-steroid type and found these compounds having outstanding anti-allergic actions with almost no side-effects both in oral and topical administration after various studies on their pharmacological acitivities. The compounds of this invention possess such pharmacological activities as anti-inflammatory anti-ulcerative, antibacterial and anti-thrombotic activities. Therefore, these compounds are useful as medicines from an industrial viewpoint. The compounds also possess a high degree of surface-activating effect and, therefore, can be used as additives for toothpaste and shampoo, as surface active agents for detergents, dispersing agents, emulsifying agents and cosmetics, and also as anticarious agents. Especially as detergents among others, they are useful as a new type of detergent to be used on persons with delicate skin or of allergic constitution, thanks to the fact that the detergents thus prepared are less toxic and milder than conventional ones in their effect on skin or mucous membranes despite their strong surface-activities and also are tasteless and odorless. Besides, the other properties, both physical and chemical, peculiar to the compounds of this invention are found applicable to other various fields and, therefore, the present invention has been brought to completion.

Enumerated hereunder are the representative compounds related with this invention:

N-(cis-4-isohexyl-1-methylcyclohexanecarbonyl)-glycine

N-(cis-4-isohexyl-1-methylcyclohexanecarbonyl)-L-alanine

N-(cis-4-isohexyl-1-methylcyclohexanecarbonyl)-DL-alanine

N-(cis-4-isohexyl-1-methylcyclohexanecarbonyl)-β-alanine

N-(cis-4-isohexyl-1-methylcyclohexanecarbonyl)-L-leucine

N-(cis-4-isohexyl-1-methylcyclohexanecarbonyl)-DL-leucine

N-(cis-4-isohexyl-1-methylcyclohexanecarbonyl)-L-isoleucine

N-(cis-4-isohexyl-1-methylcyclohexanecarbonyl)-DL-isoleucine

N-(cis-4-isohexyl-1-methylcyclohexanecarbonyl)-DL-norvaline

N-(cis-4-isohexyl-1-methylcyclohexanecarbonyl)-L-valine

N-(cis-4-isohexyl-1-methylcyclohexanecarbonyl)-DL-valine

N-(cis-4-isohexyl-1-methylcyclohexanecarbonyl)-DL-norleucine

N-(cis-4-isohexyl-1-methylcyclohexanecarbonyl)-DL-α-amino-n-butyric acid
N-(cis-4-isohexyl-1-methylcyclohexanecarbonyl)-ε-amino-n-butyric acid
$N^2$-(cis-4-isohexyl-1-methylcyclohexanecarbonyl)-L-glutamine
$N^2$-(cis-4-isohexyl-1-methylcyclohexanecarbonyl)-DL-glutamine
N-(cis-4-isohexyl-1-methylcyclohexanecarbonyl)-ε-aminocaproic acid
N-(cis-4-isohexyl-1-methylcyclohexanecarbonyl)-L-glutamic acid
N-(cis-4-isohexyl-1-methylcyclohexanecarbonyl)-DL-glutamic acid
N-(cis-4-isohexyl-1-methylcyclohexanecarbonyl)-sarcocine
N-(cis-4-isohexyl-1-methylcyclohexanecarbonyl)-L-methionine
N-(cis-4-isohexyl-1-methylcyclohexanecarbonyl)-DL-methionine
N-(cis-4-isohexyl-1-methylcyclohexanecarbonyl)-L-cystein
N-(cis-4-isohexyl-1-methylcyclohexanecarbonyl)-glycine ethyl ester
N-(cis-4-isohexyl-1-methylcyclohexanecarbonyl)-L-aspartic acid
N-(cis-4-isohexyl-1-methylcyclohexanecarbonyl)-DL-aspartic acid
N-(trans-4-isohexyl-1-methylcyclohexanecarbonyl)-glycine
N-(trans-4-isohexyl-1-methylcyclohexanecarbonyl)-L-alanine
N-(trans-4-isohexyl-1-methylcyclohexanecarbonyl)-DL-alanine
N-(trans-4-isohexyl-1-methylcyclohexanecarbonyl)-β-alanine
N-(trans-4-isohexyl-1-methylcyclohexanecarbonyl)-L-isoleucine
N-(trans-4-isohexyl-1-methylcyclohexanecarbonyl)-DL-isoleucine
N-(trans-4-isohexyl-1-methylcyclohexanecarbonyl)-DL-norvaline
N-(trans-4-isohexyl-1-methylcyclohexanecarbonyl)-L-valine
N-(trans-4-isohexyl-1-methylcyclohexanecarbonyl)-DL-valine
N-(trans-4-isohexyl-1-methylcyclohexanecarbonyl)-DL-norleucine
N-(trans-4-isohexyl-1-methylcyclohexanecarbonyl)-DL-α-amino-n-butyric acid
N-(trans-4-isohexyl-1-methylcyclohexanecarbonyl)-γ-amino-n-butyric acid
$N^2$-(trans-4-isohexyl-1-methylcyclohexanecarbonyl)-L-glutamine
$N^2$-(trans-4-isohexyl-1-methylcyclohexanecarbonyl)-DL-glutamine
N-(trans-4-isohexyl-1-methylcyclohexanecarbonyl)-sarcocine
N-(trans-4-isohexyl-1-methylcyclohexanecarbonyl)-L-methionine
N-(trans-4-isohexyl-1-methylcyclohexanecarbonyl)-DL-methionine
N-(trans-4-isohexyl-1-methylcyclohexanecarbonyl)-L-cystein
N-(trans-4-isohexyl-1-methylcyclohexanecarbonyl)-L-aspartic acid
N-(trans-4-isohexyl-1-methylcyclohexanecarbonyl)-DL-aspartic acid
N-(trans-4-isohexyl-1-methylcyclohexanecarbonyl)-glycine methyl ester
N-(cis-4-isohexylcyclohexanecarbonyl)-glycine
N-(cis-4-isohexylcyclohexanecarbonyl)-β-alanine
N-(cis-4-isohexylcyclohexanecarbonyl)-L-alanine
N-(cis-4-isohexylcyclohexanecarbonyl)-DL-alanine
N-(cis-4-isohexylcyclohexanecarbonyl)-sarcocine
$N^2$-(cis-4-isohexylcyclohexanecarbonyl)-L-glutamine
$N^2$-(cis-4-isohexylcyclohexanecarbonyl)-DL-glutamine
N-(cis-4-isohexylcyclohexanecarbonyl)-L-glutamic acid
N-(cis-4-isohexylcyclohexanecarbonyl)-DL-glutamic acid
N-(cis-4-isohexylcyclohexanecarbonyl)-ε-aminocaproic acid
N-(cis-4-isohexylcyclohexanecarbonyl)-L-cystein
N-(trans-4-isohexylcyclohexanecarbonyl)-glycine
N-(trans-4-isohexylcyclohexanecarbonyl)-L-alanine
N-(trans-4-isohexylcyclohexanecarbonyl)-DL-alanine
N-(trans-4-isohexylcyclohexanecarbonyl)-sarcocine
$N^2$-(trans-4-isohexylcyclohexanecarbonyl)-L-glutamine
$N^2$-(trans-4-isohexylcyclohexanecarbonyl)-DL-glutamine
N-(trans-4-isohexylcyclohexanecarbonyl)-L-glutamic acid
N-(trans-4-isohexylcyclohexanecarbonyl)-DL-glutamic acid
N-(trans-4-isohexylcyclohexanecarbonyl)-ε-aminocaproic acid
N-(trans-4-isohexylcyclohexanecarbonyl)-glycine isopropyl ester
N-(trans-4-isohexylcyclohexanecarbonyl)-ε-aminocaproic acid methyl ester The process for preparing the compounds of this invention is to be described below, but this is only an example and, therefore, these compounds can also be prepared by means of other chemically analogous methods.

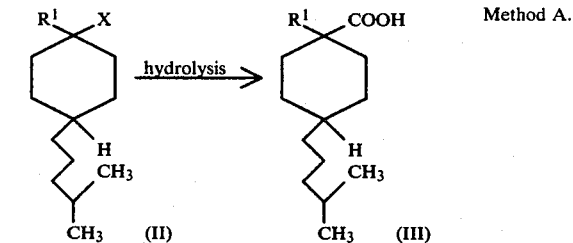

Method A.

Wherein X is selected from the group consisting of cyano, lower alkoxycarbonyl or carbomyl: $R^1$ is selected from the group consisting of hydrogen or methyl.

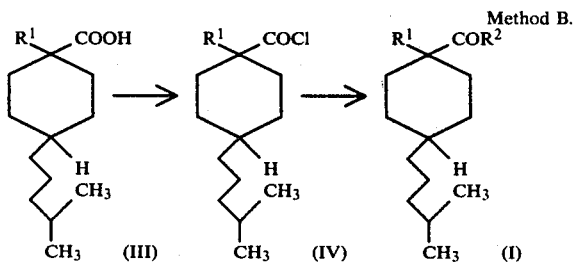

Method B.

Wherein R¹ and R² have the same meanings as previously defined.

The foregoing methods for preparing the compounds of this invention are described as follows:

The reactions in Method A, the reaction of the compounds represented by the general formula II can be made in water solution of 10–30% mineral acids (e.g. hydrochloric acid and sulfuric acid) or, for the purpose of keeping the uniformity of the reactions, in organic acids such as acetic acid using mineral acids at room temperature or, if necessary, by heating at 10°–120° C. for 3 to 5 hours. The said reactions can also be made in water solution of alkali (e.g. sodium hydroxide, potassium hydroxide, sodium carbonate and potassium carbonate) or in aqueous alcohol at room temperature or, if necessary, by heating at 10°–120° C. for 3 to 20 hours. The aforesaid acid or alkali are added in equivalent moles to in small excess to the compounds represented by the general formula II. Another conditions may be quite enough as same as common conditions of hydrolysis.

As indicated below, in the compounds (III) exist two stereogeometrical isomers, namely, cis-isomer (IIIa) and trans-isomer (IIIb),

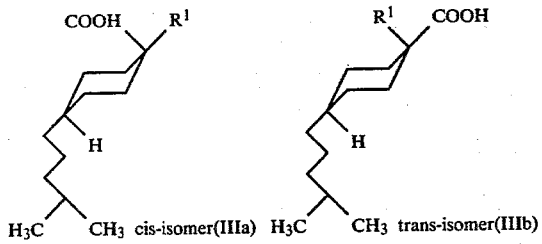

which can be separated by taking advantage of the reactivity of their functional groups and the difference of their spatial configuration (e.g. the formation of clathrate compounds consisting of urea, thiourea and cyclo-dextrine or the stability in hydrolytic reactions).

Method B can be obtained in such a way that acid halide (IV) which is attained by treating cis-isomer (IIIa) and trans-isomer (IIIb) obtained in Method A with halogenating agents (e.g. thionyl chloride, phosphorus oxychloride and phosphorus pentachloride), is made to react with the corresponding lower alcohol and amino acid.

The reactions of acid halide (IV) with lower alcohol proceed rapidly if conducted in the organic solvents (e.g. tetrahydrofuran, acetone, diglyme, chloroform, benzene and toluene) which are non-reactive in the presence of alkali (e.g. triethylamine, pyridine, sodium carbonate and potassium carboneate), at room temperature or by heating at 10°–120° C., if necessary.

The reactions with amino acid can be made by dissolving or suspending it in solvents (e.g. water, alcohol, acetone, tetrahydrofuran, dioxane and their mixture) and to the solvents are added dropwise alkali and acid halide in the quantity equivalent to or in excess of amino acid group in the presence of alkali (e.g. sodium hydroxide, potassium hydroxide, sodium carbonate, potassium carbonate, trimethylamine, triethylamine, pyridine and their mixtures). During the dropping pH in the reaction system should be kept within the range of 9–12.5 and stirred in the state of being cooled or at room temperature (5°–30° C.) and, if necessary, heated at 40°–60° C. in a water bath following the dropping. If the product thus obtained can be isolated as N-acyl amino acid, it can also be led to the production of lower alkyl ester by means of putting hydrogen chloride in lower alcohol or treating with dehydrating agents such as sulfate and dicyclohexylcarbodiimide or treating with borontrifluoride etherate. Besides, the same result can also be obtained by making amino acid derivatives react with acid anhydride, mixed acid anhydride and isopropenylester, instead of acid halide, or by heating carboxylic acid and amino acid for dehydration.

The compounds (II) which are the starting materials of this invention can be synthesized in the manner described in, for instance, Ohloff G., Justus Liebigs Annalen der Chemie, 606, 100('57).

Examples of the compounds of the present invention are shown in following Table I including their melting point or mass spectra(parent ion), appearance and solvents of recrystallization.

TABLE I

The object compounds of the present invention represented by general formula I:

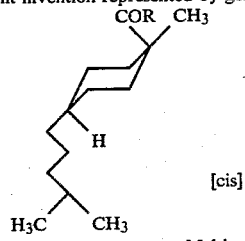

| Compound No. | R | Melting point(°C.) | appearance | solvents |
|---|---|---|---|---|
| 1 | —OH | 92–94 | colorless needles | acetonitrile |
| 2 | —NHCH₂COOH | 90–93 | colorless needles | petroleum ether |
| 3 | —NHCH₂CH₂CH₂CH₂CH₂COOH | 72–74 | colorless prisms | ether, petroleum ether |
| 4 | —NHCH₂COOC₂H₅ | 86–89 | colorless needles | acetonitrile |
| 5 | —NHCHCOOH (L form), CH₃ | 120–122 | colorless scales | acetonitrile |
| 6 | —NHCH₂CH₂COOH | 62–65 | colorless needles | " |

TABLE I-continued

| | | | | |
|---|---|---|---|---|
| 7 | CH₂CH(CH₃)CH₃<br>—NHCHCOOH (L form) | 173–175 | colorless needles | " |
| 8 | CH(CH₂CH₃)CH₃<br>—NHCHCOOH (L form) | 62–64 | colorless prisms | " |
| 9 | CH₂CH₂CH₃<br>—NHCHCOOH (DL form) | 126–128 | colorless scales | isopropyl ether |
| 10 | CH(CH₃)CH₃<br>—NHCHCOOH (L form) | 121–123 | colorless prisms | isopropyl ether |
| 11 | CH₂CH₂CH₂CH₃<br>—NHCHCOOH (DL form) | 132–133 | colorless needles | isopropyl ether |
| 12 | CH₂CH₃<br>—NHCHCOOH (DL form) | 109–112 | colorless needles | ether, petroleum ether |
| 13 | —NHCH₂CH₂CH₂COOH | 108–109 | colorless needles | ether, petroleum ether |
| 14 | CH₂CH₂CONH₂<br>—NHCHCOOH (L form) | 129–131 | colorless needles | acetonitrile |
| 15 | CH₂CH₂COOH<br>—NHCHCOOH (L form) | 133–135 | colorless needles | " |
| 16 | CH₃<br>—NCH₂COOH | 80–82 | colorless scales | " |
| 17 | CH₂CH₂SCH₃<br>—NHCHCOOH (L form) | 133–136 | colorless prism | " |
| 18 | CH₂SH<br>—NH—CH—COOH (L form) | —(m/e 329) | colorless oil | |
| 19 | COOH<br>—(—NH—CH—CH₂S)₂ (L form) | 80–82 | colorless needles | acetonitrile |

The object compounds of the present invention represented by general formula I:

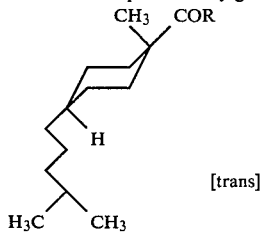

[trans]

| Compound No. | R | Melting point(°C.) | appearance | solvents |
|---|---|---|---|---|
| 20 | —OH | 51–53 | colorless prisms | acetonitrile |
| 21 | —NHCH₂COOH | 108–111.5 | colorless scales | ether, petroleum ether |
| 22 | CH₂CH₂SCH₃<br>—NHCHCOOH (L form) | 102–104 | colorless needles | petroleum ether |
| 23 | CH₂CH₂CH₂CH₃<br>—NHCHCOOH (DL form) | 109–111 | colorless needles | petroleum ether |
| 24 | CH₃<br>—NCH₂COOH | 131–132 | colorless needles | ether, isopropyl ether |
| 25 | CH₃<br>—NHCHCOOH (L form) | 114–115 | colorless scales | isopropyl ether |
| 26 | —NHCH₂CH₂COOH | 112–114 | colorless scales | isopropyl ether |

TABLE I-continued

| No. | R | Melting point (°C.) | appearance | solvents |
|---|---|---|---|---|
| 27 | —NHCHCOOH—CH(CH₂CH₃)(CH₃) (L form) | 84–86 | colorless prisms | acetonitrile |
| 28 | —NHCHCOOH—CH₂CH₂CH₃ (DL form) | 100–102 | colorless needles | petroleum ether |
| 29 | —NHCHCOOH—CH(CH₃)(CH₃) (L form) | 114–115 | colorless needles | acetonitrile |
| 30 | —NHCHCOOH—CH₂CH₃ (DL form) | 128–131 | colorless needles | petroleum ether |
| 31 | —NHCH₂CH₂CH₂COOH | 103–105 | colorless prisms | isopropyl ether |
| 32 | —NHCHCOOH—CH₂CH₂CONH₂ (L form) | 168–171 | colorless needles | ethyl acetate |
| 33 | —NCH₂COOH—CH₃ | 120–121 | colorless needles | isopropyl ether |

The object compounds of the present invention represented by general formula I:

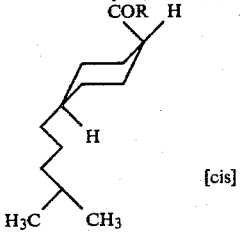

[cis]

| Compound No. | R | Melting point(°C.) | appearance | solvents |
|---|---|---|---|---|
| 34 | —NHCH₂COOH | 115–117 | white needles | petroleum ether |
| 35 | —NHCH₂CH₂COOH | 105–110 | white needles | petroleum ether |
| 36 | —NHCHCOOH—CH₃ (L form) | 132–135 | white needles | isopropyl ether |
| 37 | —NCH₂COOH—CH₃ | 105–110 | white needles | petroleum ether |
| 38 | —NHCHCOOH—CH₂CH₂COOH (L form) | 165–168 | white prisms | ethanol, isopropyl ether |
| 39 | —NHCH₂CH₂CH₂CH₂CH₂COOH | 121–124 | white needles | ethyl acetate, isopropyl ether |

The object compounds of the present invention represented by general formula I:

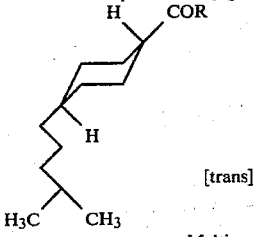

[trans]

| Compound No. | R | Melting point(°C.) | appearance | solvents |
|---|---|---|---|---|
| 40 | —NHCH₂COOH | 159–161 | colorless scales | acetone |
| 41 | —NHCHCOOH—CH₃ (L form) | 189–192 | colorless needles | ethyl acetate, ether |
| 42 | —NHCH₂CH₂CH₂CH₂CH₂COOH | 129–130 | colorless needles | acetone |
| 43 | —NHCH₂CH₂CH₂CH₂CH₂COOCH₃ | 191–193 | colorless needles | acetone, water |

The compounds of the present invention were tested for their acute toxicities, anti-allergic activities, anti-inflammatory activities and surface activities. It is found that certain of the compounds of the present invention have shown a remarkable effects in all of those tests. The testing methods are described in the following, and the results are summarized in Table II–VII.

(1) Acute toxicity

Each test compound suspended in 0.5% tragacanth gum-saline was administered orally, subcutaneously or intraperitoneally to animals ddY strain mouse and Wistar strain rats. The 50% lethal dose and the 95% confidence limit were calculated by Litchfield-Wilcoxon's method from the death of animals in 3 weeks following administration.

TABLE II

| Test compound | animal | $LD_{50}$ values (mg/kg) | | |
|---|---|---|---|---|
| | | p.o. | s.c. | i.p. |
| Compound No. 1 | male rat | >10000 | >10000 | 2070 (1780–2400) |
| | female rat | >10000 | >10000 | 1690 (1470–1940) |
| | male mouse | 5950 (4960–7140) | >10000 | 1110 (982–1254) |
| | female mouse | 6390 (5685–7182) | >10000 | 998 (903–1103) |
| | male dog | >5000 | | |
| | female dog | >5000 | | |
| | male rabbit | >6000 | | |
| | female rabbit | >6000 | | |
| Compound No. 2 | male rat | ≈11000 | | |
| | female rat | ≈10300 | | |

(2) Homologeous passive cutaneous anaphylaxis in rat

Each test compound suspended in 0.5% tragacanth gum-distilled water was administered orally to a group of five male Wistar strain rats (body weight 150–200 g). After one hour 0.1 ml of 5% anti-Dinitrophinol conpled Ascaris rat IgE serum-physiological sodium chloride solution was injected intradermally to dorsum of the rat. After 48 hours, 1 ml saline solution dissolved DNP-Ascaris (protein concentration 2 mg/ml) and 0.25% Evans blue was injected intravenously. The animals were sacrificed by decapitation 30 minutes after the injection. Thereafter the skin of the animals were removed and the amount of the pigment exuded into the inflamed skin was determined. The percent inhibitions were calculated by the ratio of the amounts of exuded pigments to the control.

TABLE III

| Test compound | Dose(mg/kg) | Inhibition(%) |
|---|---|---|
| Compound No. 1 | 100 | 28 |
| Compound No. 2 | 100 | 46 |
| Glycyrrhizin | 100 | 22 |
| Prednisolone | 5 | 42 |

(3) Picryl Chloride induced contact dermatitis

At first 0.1 ml of 7% picryl chloride-ethanol solution was applied to skin of the depilated abdomens (area 2.5×15 mm) of ddY-strain male mice (body weight 20–22 g). After one week each 0.02 ml of 1% picryl chloride-olive oil solution was applied topically to the ears of the mouse. The ears the selected mice swelled well enough. After three days 0.1 ml of 7% picryl chloride-ethanol solution was applied again to the depilated abdomens of the mice. After one week, each 0.02 ml of 1% picryl chloride-olive oil solution per ear were applied topically to the bilateral ears, and at same time, the test compounds were administered orally. Immediately before and 24 hours after the second challenge, the thickness of the ears was measured and the swelling was calculated. The percent inhibitions were calculated by the ratio of the each swelling to the control.

TABLE IV

| Test compound | Dose (mg/kg) | Inhibition(%) |
|---|---|---|
| Compound No. 1 | 100 | 49 |
| 2 | 100 | 41 |
| 3 | 100 | 45 |
| 5 | 100 | 32 |
| 6 | 100 | 10 |
| 8 | 100 | 41 |
| 9 | 100 | 47 |
| 10 | 100 | 9 |
| 11 | 100 | 37 |
| 12 | 100 | 27 |
| 13 | 100 | 40 |
| 14 | 100 | 7 |
| 17 | 100 | 50 |
| 18 | 100 | 27 |
| 20 | 100 | 44 |
| 21 | 100 | 53 |
| Prednisolone | 5 | 32 |

(4) Mediator release on lung fragment of guinea pig.

A group of Hartley strain male guinea pigs (body weight 250–300 g) were administered intraperitoneally anti-BPO-BGG IgE serum. The animals were sacrificed by decapitation, and those sensitized lungs were isolated for use. 500 mg of the fragments of the sensitized lungs were immersed in the 4.5 ml of Tyrode's solution. Thereafter, the immersed solution preincubated for five minutes at 37° C. were added to 0.25 ml of test compounds dissolved or suspended Tyrode's solution, and at three minutes thereafter, BPO-BSA at the final concentration of $10^{-6}$ g/ml. Following 10 minute incubation, the amount of the released histamine were determined by bioassay.

TABLE V

| Test compound | concentration g/ml) | inhibition (%) |
|---|---|---|
| Compound No. 1 | $10^{-4}$ | 24.2 |
| Compound No. 2 | $10^{-4}$ | 73.0 |
| Glycyrrhizin | $10^{-4}$ | 8.0 |
| Prednisolone | $10^{-4}$ | 4.0 |

(5) Effect on rat adjuvant polyarthritis

A group of eight to ten male Sprague Dawley strain rats (body weight 240–280 g) were used. 0.1 ml of Complete Freuind's adjuvant (CFA, Mycobacterium butyricum, 100 mg/10 cc) was injected intradermally to the right hind sole. The animals were given orally the test compound, 200 mg/kg at daily for 21 days after the injection, and the each swelling of the bilateral hind paw was measured at Ibuprofen which was orally administered at a dose of 50 mg/kg/day and Prednisolone which was orally administered at a dose of 0.5 mg/kg/day were administered as reference medicines.

TABLE VI-I

| Swelling percent (%) of right hind paw (treatment of CFA) | | | | |
|---|---|---|---|---|
| | Test compound | | | |
| day | Control | Compound No. 1 | Ibuprofen | Prednisolone |
| 0 | 118.1± 4.3 | 118.1± 5.0 | 118.6± 5.7 | 118.4± 6.0 |
| 1 | 98.7±5.1 | 100.0± 5.3 | 98.1± 6.1 | 97.3± 6.5 |
| 4 | 279.4±13.5 | 255.4±13.8 | 204.7±11.6** | 232.7±17.8 |
| 7 | 242.1±16.7 | 216.3±12.8 | 181.7±14.8* | 200.3±22.5 |
| 10 | 209.1±15.5 | 173.8± 7.1 | 160.5±12.2* | 167.2±19.0 |
| 14 | 201.4±17.5 | 169.5± 8.0 | 163.0±11.1 | 175.0±18.6 |

TABLE VI-I-continued

Swelling percent (%) of right hind paw (treatment of CFA)

| | Test compound | | |
|---|---|---|---|
| day Control | Compound No. 1 | Ibuprofen | Prednisolone |
| 17 206.8±18.7 | 166.0± 8.6 | 152.5±11.8* | 174.2±18.6 |
| 21 210.9±19.3 | 163.0±10.5* | 138.5±12.6** | 173.0±23.7 |

TABLE VI-II

Swelling percent (%) of left hind paw (non-treatment of CFA)

| | Test compound | | |
|---|---|---|---|
| day Control | Compound No. 1 | Ibuprofen | Prednisolone |
| 0  −0.4±1.7 | −1.3±1.8 | −1.7±1.3 | −1.1±1.0 |
| 1  −0.3±1.2 | −3.0±1.2 | −2.4±1.0 | −1.0±1.0 |
| 4  −2.3±1.8 | −0.8±2.0 | −2.3±1.5 | −1.7±1.1 |
| 7   8.4±2.0 | 4.5±3.3 | 1.5±1.8* | 5.7±1.9 |
| 10  7.8±3.0 | 11.8±2.4 | 7.4±1.8 | 4.5±2.9 |
| 14 17.2±2.2 | 13.3±1.6 | 12.5±1.5 | 12.5±2.4 |
| 17 23.4±2.5 | 13.2±1.7** | 8.5±1.5** | 9.8±1.4** |
| 21 21.3±4.4 | 8.5±2.0* | 8.5±2.0* | 7.1±1.5* |

The symbols, * and ** represent the significant difference fromcontrol, * at 5%; ** at 1%.

(6) Emulsification test and determination of surface tention

N-acyl-L-glutamic acid salt (Tradename: Amisoft) is a good surfactant which is generally used in the fields of perfumery or industry nowadays as its safety and biodegradation activity.

As the structure of the compounds of the present invention is comparatively, similar to Amisoft, HS-11, a sort of Amisoft, which is mixture of 70% of N-stearoyl-L-glutamic acid monosodium salt and 30% of N-palmitoyl-L-glutamic acid monosodium salt was selected for the tests. The surface activity and the surface tension of the said HS-11 and the compounds of the present invention were measured and determined respectively, and those comparative results were shown in Table VII.

(1) Emulsification test.

10 ml of the 0.25% solution of the salt of each compound was added to the 10 ml of toluene. They were emulsified in the test tube by turning it upside down repeatedly for 30 times at 40° C. and were allowed to stand for 15 minutes. After the standing the separated volume of aqueous layer was measured.

(2) Determination of surface tension

The 0.25% solution of the salt of each compound was determined by Ring method at 25° C.

TABLE VII

| Test compound | Separated volume of aqueous layer (ml) | Surface tension γ(dyn/cm) |
|---|---|---|
| Compound No. 2 (potassium salt) | 9.5 | 39.5 |
| Compound No. 12 (potassium salt) | 7.3 | 44.5 |
| Compound No. 15 (monosodium salt) | 9.3 | 42.3 |
| Compound No. 17 (triethanolamine salt) | 9.5 | 42.3 |
| Compound No. 42 (sodium salt) | 9.5 | 38.8 |
| Amisoft[HS-11] | 9.3 | 44.7 |

Example of the present invention are illustrated in the following.

EXAMPLE 1

A mixture of 120 g of cis and trans-4-isohexyl-1-methylcyclohexanecarbonyl-methyl ester (the ratio of cis-isomer and trans-isomer is 7:3) is heated along with 7 g of sodium hydroxide in 500 ml of hydrous methanol at 50°–55° C. for 3 hours. After the reaction, the reaction solvent is distilled off from the mixture under reduced pressure. The residue thus obtained is extracted with ether several times with some iced water added. The aqueous layer is made acid with diluted hydrochloric acid and the crude crystals precipitated are collected by filtration and then washed and dried. The recrystallization of these crystals from acetonitrile yields 26 g of trans-4-isohexyl-1-methylcyclohexanecarboxylic acid as colorless prisms, melting at 51°–53° C. Furthermore, after ether is distilled away the ether layer is added to a solution of 62 g of potassium hydroxide and 700 ml of methanol, and then the mixture is refluxed for 5 hours. After the reaction, the reaction solvent is distilled off from the mixture under reduced pressure. With some iced water added, the residue thus obtained is made acid with hydrochloric acid and the crude crystals precipitated are collected by filtration and then washed and dried. The recrystallization of these crystals from acetonitrile yielded 70 g of cis-4-isohexyl-1-methylcyclohexanecarboxylic acid as colorless needles, melting at 92°–94° C.

EXAMPLE 2

To a solution of 30 g of cis-4-isohexyl-1-methylcyclohexanecarboxylic acid and 150 cc of benzene is added 30 g of phosphorus pentachloride and the mixture is allowed to stand for 30 minutes at room temperature and then refluxed for 1 hour. After the reaction was finished, the reaction solvent was distilled off from the mixture under reduced pressure for producing 33.5 g of cis-4-isohexyl-1-methylcyclohexanecarbonyl chloride. To a solution of 11 g of glycine and 100 ml of distilled water are added 11.7 g of sodium hydroxide and 21 cc of water in the state of being cooled and stirred, and then the mixture and the aforesaid acid chloride are made to drop alternately. During the dropping, pH of the solvent is kept within 9–12.5. After the dropping the solvent is stirred for 3 hours at room temperature. After the reaction is finished, pH 2 is prepared by adding diluted hydrochloric acid to the reaction mixture and then extracted with ether. Ether was distilled away following the washing and dehydration of the ether layer, and the residue thus obtained was recrystallized from petroleum ether to yield 37 g of N-(cis-4-isohexyl-1-methylcyclohexanecarbonyl)-glycine as colorless needles, melting at 90°–93° C.

EXAMPLE 3

To a solution of 12.7 g of trans-4-isohexyl-1-methylcyclohexanecarboxylic acid and 50 ml of benzene is added 11.6 g of phosphorus pentachloride and the mixture is allowed to stand for 30 minutes at room temperature and then refluxed for 1 hour. After the reaction was finished, the reaction solvent was distilled off from the mixture under reduced pressure for producing 13.2 g of trans-4-isohexyl-1-methylcyclohexancecarbonyl chloride. To a solution of 4.3 g of glycine and 30 ml of distilled water are added 4.5 g of sodium hydroxide and 10 ml of water in the state of being cooled and stirred, and then the mixture and the aforesaid acid chloride are made to drop alternately. During the dropping, pH of the solvent is kept within 9–12.5. After the dropping the solvent is stirred for 3 hours at room temperature. After the reaction is finished, pH 2 is prepared by adding diluted hydrochloric acid to the reaction mixture and then extracted with ether. The ether layer was washed and dehydrated, and then the solvent was distilled away. The residue thus obtained was recrystallized from the mixed solvent of ether and petroleum ether to yield 14.5 g of N-(trans-4-isohexyl-1-methylcyclohexanecarbonyl)-glycine as colorless scales, melting at 108°–111.5° C.

EXAMPLE 4

To a solution of 6.3 g of ε-aminocaproic acid and 40 ml of distilled water is added 3.6 g of sodium hydroxide dissolved in 8 ml of water in the state of being cooled and stirred, and then the mixture and 10.5 g of cis-4-isohexyl-1-methylcyclohexanecarbonyl chloride are made to drop alternately. During the dropping, pH of the solvent is kept within 9–12.5. After the dropping the solvent is kept at room temperature for 3 hours and then warmed at 50° C. for 15 minutes. After the reaction is finished, pH 2 is prepared by adding diluted hydrochloric acid to the reaction mixture and then extracted with glacial acetic acid ethyl ester. The glacial acetic acid ethyl ester layer was washed and dehydrated, and then the solvent was distilled away. The residue thus obtained was recrystallized from the mixed solvent of ether and petroleum ether to yield 10.5 g of N-(cis-4-isohexyl-1-methylcyclohexanecarbonyl)-ε-aminocaproic acid as colorless prisms, melting at 72°–74° C.

EXAMPLE 5

To a solution of 4.6 g of L-methionine, 5 g of sodium carbonate and 40 ml of water is added 2.5 g of sodium hydroxide dissolved in 8 ml of water in the state of being cooled and stirred, and then the mixture and 7.6 g of trans-4-isohexyl-1-methylcyclohexanecarbonyl chloride are made to drop alternately. During the dropping, pH of the solvent is kept within 9–12.5. After the dropping the solvent is kept at room temperature for 3 hours and then warmed at 50° C. for 15 minutes. After the reaction is finished, pH 2 is prepared by adding diluted hydrochloric acid to the reaction mixture and then extracted with ether. The ether layer was washed and dehydrated, and then the solvent was distilled away. The residue thus obtained was recrystallized from petroleum ether to yield 8.8 g of N-(trans-4-isohexyl-1-methylcyclohexanecarbonyl)-L-methionine as colorless needles, melting at 102°–104° C.

EXAMPLE 6

To a solution of 4.1 g of DL-norleucine, 5 g of sodium carbonate and 40 ml of water is added 2.5 g of sodium hydroxide dissolved in 8 ml of water in the state of being cooled and stirred, and then the mixture and 7.6 g of trans-4-isohexyl-1-methylcyclohexanecarbonyl chloride are made to drop alternately. During the dropping, pH of the solvent is kept within 9–12.5. After the dropping the solvent is kept at room temperature for 3 hours and then warmed at 50° C. for 15 minutes. After the reaction is finished, pH 2 is prepared by adding diluted hydrochloric acid to the reaction mixture and then extracted with ether. The ether layer was washed and dehydrated, and then the solvent was distilled away. The residue thus obtained was recrystallized from petroleum ether to yield 9.4 g of N-(trans-4-isohexyl-1-methylcyclohexanecarbonyl)-DL-norleucine as colorless needles, melting at 109°–111° C.

EXAMPLE 7

To a solution of 3.4 g of sarcocine, 6 g of sodium carbonate and 40 ml of water is added 3.2 g of sodium hydroxide dissolved in 8 ml of water in the state of being cooled and stirred, and then the mixture and 8.7 g of trans-4-isohexylcyclohexanecarbonyl chloride are made to drop alternately. During the dropping, pH of the solvent is kept within 9–12.5. After the dropping the solvent is kept at room temperature for 3 hours and then warmed at 50° C. for 15 minutes. After the reaction is finished, pH 2 is prepared by adding diluted hydrochloric acid to the reaction mixture and then extracted with ether. The ether layer was washed and dehydrated, and then the solvent was distilled away. The residue thus obtained was recrystallized from the mixed solvent of ether and isopropyl ether to yield 9.5 g of N-(trans-4-isohexylcyclohexanecarbonyl)-sarcocine as colorless needles, melting at 131°–132° C.

EXAMPLE 8

To a solution of 20 g of glycine ethyl ester, 15 g of triethylamine and 100 ml of tetrahydrofuran is added dropwise slowly 23.4 g of cis-4-isohexyl-1-methylcyclohexanecarbonyl chloride at ice-cold temperature. After the dropping the solvent is stirred for 3 hours at room temperature. After the reaction is finished, triethylamine hydrochloric acid salt is collected by filtration. The reaction solvent was distilled off from the filtrate under reduced pressure to give a residue, to which was added some iced water. The crude crystals precipitated were collected by filtration and dried. Recrystallization of these crystals from acetonitrile yielded 30 g of N-(cis-4-isohexyl-1-methylcyclohexanecarbonyl)-glycine ethyl ester as colorless needles, melting at 86°–89° C.

EXAMPLE 9

To a solution of 4.6 g of glycine and 70 ml of water was added 10 g of cis-4-isohexyl-1-methylcyclohexanecarbonyl chloride in the state of being stirred, and then was added dropwise 13 g of triethylamine at room temperature. After the dropping the mixture was stirred for 1 hour and allowed to react for 30 minutes at 50° C. After the reaction was finished, pH 2 was prepared by adding diluted hydrochloric acid to the reaction mixture and then extracted with ether. The ether layer was washed and dehydrated, and then ether was distilled away. The residue thus obtained was recrystallized from petroleum ether to yield 11 g of N-(cis-4-isohexyl-1-methylcyclohexanecarbonyl)-glycine as colorless needles, melting at 90°–93° C.

What is claimed is:

1. A compound of the formula:

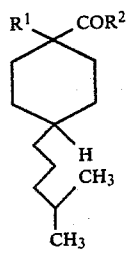

wherein R¹ is hydrogen or methyl and R² is amino acid rest which is selected from the group consisting of the rest of glutamic acid, aspartic acid, α-aminoadipic acid, α-aminopimelic acid, glutamine, cysteic acid, homocysteic acid, 2-aminoeicosandicarboxylic acid, glycine, phenylalanine, phenylalanine, phenylglycine, alanine, α-aminobutyric acid, valine, norvaline, leucine, isoleucine, norleucine, p-nitro-phenylalanine, methionine, cystein, homocystine, penicillamine, ethionine or a lower alkyl ester thereof; threonine, serine, β-hydroxyleucine, or homoserine; the N-methyl or N-ethyl derivative of sarcocine; the o-acyl or o-methyl derivative of serine; a N$^\omega$,N$^\omega$-dilower alkyl derivative of lysine, or a N$^\omega$, N$^\omega$-dilower alkyl derivative of ornithine; β-alanine, or β-aminoisobutyric acid; and γ-aminovaleraic acid, ε-aminocaproic acid or the N-methyl or N-ethyl derivative thereof.

2. A compound in accordance with claim 1 selected from the group consisting of:

N-(cis-4-isohexyl-1-methylcyclohexanecarbonyl)-glycine,
N-(cis-4-isohexyl-1-methylcyclohexanecarbonyl)-L-alanine,
N-(cis-4-isohexyl-1-methylcyclohexanecarbonyl)-DL-alanine,
N-(cis-4-isohexyl-1-methylcyclohexanecarbonyl)-β-alanine,
N-(cis-4-isohexyl-1-methylcyclohexanecarbonyl)-L-leucine,
N-(cis-4-isohexyl-1-methylcyclohexanecarbonyl)-DL-leucine,
N-(cis-4-isohexyl-1-methylcyclohexanecarbonyl)-L-isoleucine,
N-(cis-4-isohexyl-1-methylcyclohexanecarbonyl)-DL-isoleucine,
N-(cis-4-isohexyl-1-methylcyclohexanecarbonyl)-DL-norvaline,
N-(cis-4-isohexyl-1-methylcyclohexanecarbonyl)-L-valine,
N-(cis-4-isohexyl-1-methylcyclohexanecarbonyl)-DL-valine,
N-(cis-4-isohexyl-1-methylcyclohexanecarbonyl)-DL-norleucine,
N-(cis-4-isohexyl-1-methylcyclohexanecarbonyl)-DL-α-amino-n-butyric acid,
N-(cis-4-isohexyl-1-methylcyclohexanecarbonyl)-ε-amino-n-butyric acid,
N²-(cis-4-isohexyl-1-methylcyclohexanecarbonyl)-L-glutamine,
N²-(cis-4-isohexyl-1-methylcyclohexanecarbonyl)-DL-glutamine,
N-(cis-4-isohexyl-1-methylcyclohexanecarbonyl)-ε-aminocaproic acid,
N-(cis-4-isohexyl-1-methylcyclohexanecarbonyl)-L-glutamic acid,
N-(cis-4-isohexyl-1-methylcyclohexanecarbonyl)-DL-glutamic acid,
N-(cis-4-isohexyl-1-methylcyclohexanecarbonyl)-sarcocine,
N-(cis-4-isohexyl-1-methylcyclohexanecarbonyl)-L-methionine,
N-(cis-4-isohexyl-1-methylcyclohexanecarbonyl)-DL-methionine,
N-(cis-4-isohexyl-1-methylcyclohexanecarbonyl)-L-cystein,
N-(cis-4-isohexyl-1-methylcyclohexanecarbonyl)-glycine ethyl ester,
N-(cis-4-isohexyl-1-methylcyclohexanecarbonyl)-L-aspartic acid,
N-(cis-4-isohexyl-1-methylcyclohexanecarbonyl)-DL-aspartic acid,
N-(trans-4-isohexyl-1-methylcyclohexanecarbonyl)-glycine,
N-(trans-4-isohexyl-1-methylcyclohexanecarbonyl)-L-alanine,
N-(trans-4-isohexyl-1-methylcyclohexanecarbonyl)-DL-alanine,
N-(trans-4-isohexyl-1-methylcyclohexanecarbonyl)-β-alanine,
N-(trans-4-isohexyl-1-methylcyclohexanecarbonyl)-L-isoleucine,
N-(trans-4-isohexyl-1-methylcyclohexanecarbonyl)-DL-isoleucine,
N-(trans-4-isohexyl-1-methylcyclohexanecarbonyl)-DL-norvaline,
N-(trans-4-isohexyl-1-methylcyclohexanecarbonyl)-L-valine,
N-(trans-4-isohexyl-1-methylcyclohexanecarbonyl)-DL-valine,
N-(trans-4-isohexyl-1-methylcyclohexanecarbonyl)-DL-norleucine,
N-(trans-4-isohexyl-1-methylcyclohexanecarbonyl)-DL-α-amino-n-butyric acid,
N-(trans-4-isohexyl-1-methylcyclohexanecarbonyl)-γ-amino-n-butyric acid,
N²-(trans-4-isohexyl-1-methylcyclohexanecarbonyl)-L-glutamine,
N²-(trans-4-isohexyl-1-methylcyclohexanecarbonyl)-DL-glutamine,
N-(trans-4-isohexyl-1-methylcyclohexanecarbonyl)-sarcocine,
N-(trans-4-isohexyl-1-methylcyclohexanecarbonyl)-L-methionine,
N-(trans-4-isohexyl-1-methylcyclohexanecarbonyl)-DL-methionine,
N-(trans-4-isohexyl-1-methylcyclohexanecarbonyl)-L-cystein,
N-(trans-4-isohexyl-1-methylcyclohexanecarbonyl)-L-aspartic acid,
N-(trans-4-isohexyl-1-methylcyclohexanecarbonyl)-DL-aspartic acid,
N-(trans-4-isohexyl-1-methylcyclohexanecarbonyl)-glycine methyl ester,
N-(cis-4-isohexylcyclohexanecarbonyl)-glycine,
N-(cis-4-isohexylcyclohexanecarbonyl)-β-alanine,
N-(cis-4-isohexylcyclohexanecarbonyl)-L-alanine,
N-(cis-4-isohexylcyclohexanecarbonyl)-DL-alanine,
N-(cis-4-isohexylcyclohexanecarbonyl)-sarcocine,
N²-(cis-4-isohexylcyclohexanecarbonyl)-L-glutamine,
N²-(cis-4-isohexylcylohexanecarbonyl)-DL-glutamine,
N-(cis-4-isohexylcyclohexanecarbonyl)-L-glutamic acid, N-(cis-4-isohexylcyclohexanecarbonyl)-DL-glutamic acid,
N-(cis-4-isohexylcyclohexanecarbonyl)-ε-aminocaproic acid,
N-(cis-4-isohexylcyclohexanecarbonyl)-L-cystein,
N-(trans-4-isohexylcyclohexanecarbonyl)-glycine,
N-(trans-4-isohexylcyclohexanecarbonyl)-L-alanine,
N-(trans-4-isohexylcyclohexanecarbonyl)-DL-alanine,
N-(trans-4-isohexylcyclohexanecarbonyl)-sarcocine,
$N^2$-(trans-4-isohexylcyclohexanecarbonyl)-L-glutamine,
$N^2$-(trans-4-isohexylcyclohexanecarbonyl)-DL-glutamine,
N-(trans-4-isohexylcyclohexanecarbonyl)-L-glutamic acid,
N-(trans-4-isohexylcyclohexanecarbonyl)-DL-glutamic acid,
N-(trans-4-isohexylcyclohexanecarbonyl)-ε-aminocaproic acid,
N-(trans-4-isohexylcyclohexanecarbonyl)-glycine isopropyl ester and
N-(trans-4-isohexylcyclohexanecarbonyl)-ε-aminocaproic acid methyl ester.

3. A compound in accordance with claim 1 comprising N-(4-isohexyl-1-methylcyclohexanecarbonyl)-glycine.

* * * * *